United States Patent
Cohen et al.

(10) Patent No.: US 6,600,954 B2
(45) Date of Patent: Jul. 29, 2003

(54) METHOD AND APPARATUS FOR SELECTIVE CONTROL OF NERVE FIBERS

(75) Inventors: Ehud Cohen, Ganei Tikva (IL); Shai Ayal, Jerusalem (IL)

(73) Assignee: Biocontrol Medical BCM Ltd., Yahnud (IL)

( * ) Notice: Subject to any disclaimer, the term of this patent is extended or adjusted under 35 U.S.C. 154(b) by 17 days.

(21) Appl. No.: 09/824,682

(22) Filed: Apr. 4, 2001

(65) Prior Publication Data

US 2002/0099419 A1 Jul. 25, 2002

Related U.S. Application Data

(60) Provisional application No. 60/263,834, filed on Jan. 25, 2001.

(51) Int. Cl.[7] .................................................. A61N 1/34
(52) U.S. Cl. ....................................................... 607/46
(58) Field of Search .......................... 607/1, 2, 39–41, 607/46, 48, 49, 74, 116–118

(56) References Cited

U.S. PATENT DOCUMENTS 4,608,985 A * 9/1986 Crish et al. ................... 607/74

FOREIGN PATENT DOCUMENTS

WO WO 01/10375 8/2000

OTHER PUBLICATIONS

Baratta et al, "Orderly Stimulation of Skeletal Muscle Motor Units with Tripolar Nerve Cuff Electrode", *IEEE Trans Biomed. Eng.*, 38(8):836–843, 1989.

Rattay, F., Analysis for Extracellular Fiber Stimulation, *IEEE Trans Biomed. Eng.*, 36(7):676–682, 1989.

Rijkhoff et al, "Orderly Recruitment of Motoneurons in an Acute Rabbit Model", *IEEE Eng. In Medicine & Biol.*, 20(5):2564–2565, 1998.

Rijkhoff et al, "Acute Animal Studies on the Use of an Anodal Block to Reduce Urethral Resistance in Sacral Root Stimulation", *IEEE Rehabilitation Eng.*, 2(2):92–99, 1994.

Fitzpatrick et al, "A Nerve Cuff Design for the Selective Activiation and Blocking of Myelinated Nerve Fibres", *IEEE Eng. In Medicine & Biol.*, 13(2):0906–0907, 1991.

Van Den Honert et al, "A Technique for Collision Block of Peripheral Nerve: Single Stimulus Analysis", *IEEE Trans Biomed. Eng.*, BME–28(5):373–378, 1981.

Devor, M., "Pain Networks", *Handbook of Brain Theory and Neural Networks*. Ed. M.A. Arbib, MIT Press, pp 698–702, 1998.

* cited by examiner

*Primary Examiner*—George R. Evanisko
(74) *Attorney, Agent, or Firm*—G. E. Ehrlich (1995) Ltd.

(57) ABSTRACT

A method and apparatus particularly useful for pain control by selectively blocking the propagation of body-generated action potentials travelling through a nerve bundle by using a tripolar electrode device to generate unidirectional action potentials to serve as collision blocks with the body-generated action potentials representing pain sensations in the small-diameter sensory fibers. In the described preferred embodiments there are a plurality of electrode devices spaced along the length of the nerve bundle which are sequentially actuated with delays corresponding to the velocity of propagation of the body-generated action potentials through the large-diameter fibers to produce a "green wave" effect which minimizes undesired anodal blocking of the large-diameter fibers while maximizing the collision blocking of the small-diameter fibers.

28 Claims, 9 Drawing Sheets

METHOD AND APPARATUS FOR SELECTIVE CONTROL OF NERVE FIBERS

RELATED APPLICATION

This application is related to Provisional Application No. 60/263,834 filed Jan. 25, 2001, which is incorporated herein for reference and claims priority of that application.

FIELD AND BACKGROUND OF THE INVENTION

The present invention relates to the selective control of nerve fibers in the human nervous system. The invention is especially useful for selectively blocking sensory nerve fibers for blocking pain sensations while permitting other sensations to pass, and is therefore particularly described below with respect to this application. However, as will also be described below the invention could also be used in other applications, e.g., in selectively blocking motor nerve fibers for controlling muscles or glands.

The nervous system is a network of billions of interconnected nerve cells (neurons) that receive various types of stimuli and cause the body to respond appropriately. The individual nerve cells transmit the messages by means of a complicated electrochemical process which generates action potentials transmitted by axons, or nerve fibers. Such nerve fibers link the central nervous system (CNS) consisting of the brain and the spinal cord, with the body's receptors and effectors in the peripheral nervous system (PNS). The receptors are sensory cells and organs responding to various types of stimulation, such as touch, pain, light, etc., which transmit action potentials through the sensory nerve fibers towards the CNS; whereas effectors are parts of the body, such as muscles and glands, that respond to instructions from the CNS transmitted via action potentials through motor nerve fibers to effect a particular activity in such muscles or glands.

Pain sensations have the useful purpose of alerting a person as to a condition, such as heat or cold, which can be injurious to the individual. However, there are many types of pains which do not serve this useful purpose and can cause severe discomfort or distress. For example, it is estimated that chronic pain partially or totally disables 50 million persons in the USA alone, and that 45% of the population seeks medical help for persistent pain at some point in their lives. Medical economists estimate that pain costs the U.S. some $100 billion every year, including 515 million workdays lost and 40 million doctors visits.

The most widely used controls for pain at the present time are narcotic treatments. The narcotics most commonly prescribed not only have a number of worrisome side effects, but are of limited effectiveness for millions of persons who suffer from neuropathic pain arising from damage to the nerves caused by disease, trauma or chemotherapy.

Some degree of pain control may also be effected by electrical stimulation. Current technology for pain control using electrical stimulation is based on the "gate theory of pain"; see for example M. Devor, "Pain Networks", Handbook of Brain Theory and Neural Networks, Ed. M. A. Arbib, MIT Press, pp 698, 1998. This approach exploits the observation that pain sensations diminish when accompanied by a non-painful stimulus, such as the relief sensed when rubbing a painful area. Pain sensations are carried by the small-diameter nerve fibers (nociceptors), while normal sensations (such as touch) are carried by the large-diameter nerve fibers. To reduce pain, current techniques apply a low amplitude current which stimulates only the large-diameter fibers, since stimulation of the small-diameter fibers would induce pain. This is done in two ways: (a) Transcutaneous Electric Stimulation (TENS) by applying a small current externally to the skin; and (b) Dorals Column Stimulation (DCS), by inserting an electrode into the dorsal column and implanting a stimulating device nearby. This technique for pain control, however, has had a very limited degree of success.

A number of blocking techniques are also presently known for blocking or stimulating motor nerves controlling muscular or glandular activities. These include: (1) collision blocking; (2) high frequency blocking; and (3) anodal blocking.

In collision blocking, a unidirectional action potential is generated by external electrodes to travel towards the muscle or gland being controlled, i.e., from the CNS towards the PNS. These electrode-generated action potentials collide with, and thereby block, the body-generated action potentials.

In high frequency blocking, high frequency (e.g., 600 Hz) stimulations are used to block the transmission of the action potentials through the nerve fibers.

In anodal blocking, nerve fibers are locally hyper-polarized by anodal current. If sufficiently hyper-polarized, action potentials are not able to propagate through the hyper-polarized zone and will be blocked.

As will be described more particularly below, the anodal block has been investigated for producing a selective blocking of the action potentials through selected motor nerve fibers, particularly the larger-diameter nerve fibers which are more sensitive to the hyper-polarization. The unblocked electrode-generated action potentials (or those blocked to a lesser degree) passing through the anodal block are used, by collision blocking, for the selective control of motor nerve fibers in order to stimulate or suppress, as the case may be, selected muscular or glandular activities; see for example C. van den Honert, J. T. Mortimer "A Technique for Collision Blocks of Peripheral Nerve: Single Stimulus Analysis", IEEE Transactions on Biomedical Engineering, Vol. 28, No. 5, pp 373, 1981, herein incorporated by reference.

The anodal blocking technique has been investigated for stimulating various motor nerves, e.g., for the restoration of bladder and urethral sphincter control, for skeletal muscle control, etc.; see for example D. M. Fitzpatrick et al., "A Nerve Cuff Design for the Selective Activation and Blocking of Myelinated Nerve Fibers", Ann. Conf. of the IEEE Eng. in Medicine and Biology Soc., Vol. 13, No. 2, pp. 906, 1991, describing a tripolar electrode device useful for this purpose. Also see N. J. M. Rijkhof et al., "Acute Animal Studies on the Use of Anodal Block to Reduce Urethral Resistance in Sacral Root Stimulation" IEEE Transactions on Rehabilitation Engineering, Vol. 2, No. 2, pp. 92, 1994; N. J. M. Rijkhoff et al., "Orderly Recruitment of Motoneurons in an Acute Rabbit Model" Ann. Conf. of the IEEE Eng., Medicine and Biology Soc., Vol. 20, No. 5, pp. 2564, 1998; and R. Bratta et al., "Orderly Stimulation of Skeletal Muscle Motor Units with Tripolar Nerve Cuff Electrode", IEEE Transactions on Biomedical Engineering, Vol. 36, No. 8, pp. 836, 1989. The contents of the foregoing publications are incorporated herein by reference.

As described particularly in the above-cited Fitzpatrick et al publication, the tripolar electrode used for muscle control includes a central cathode flanked on its opposite sides by two anodes. The central cathode generates action potentials in the motor nerve fiber by cathodic stimulation; one anode produces a complete anodal block in one direction so that the action potential produced by the cathode is unidirectional; and the other anode produces a selective anodal block to permit passage of the action potential in the opposite direction through selected motor nerve fibers to produce the desired muscle stimulation or suppression. Further details concerning the construction and operation of such tripolar electrodes are set forth in the above-cited publications incorporated herein by reference.

OBJECTS AND BRIEF SUMMARY OF THE PRESENT INVENTION

An object of the present invention is to provide novel methods of selective control of nerve fibers which method is particularly useful for reducing pain sensations. Another object is to provide a method of selectrive control of nerve fibers which is also useful for controlling certain types of muscular or glandular activities. A further object of the invention is to provide apparatus for use in the above methods.

According to one aspect of the present invention, there is provided a method of reducing pain sensations resulting from the propagation of body-generated action potentials towards the central nervous system through small-diameter sensory fibers in a nerve bundle, without unduly reducing other sensations resulting from the propagation of body-generated action potentials towards the central nervous system through large-diameter sensory fibers in the nerve bundle, comprising: applying to the nerve bundle at least one electrode device capable, upon actuation, of generating unidirectional action potentials to be propagated through both the small-diameter and large-diameter sensory fibers in the nerve bundle away from the central nervous system; and actuating the electrode device to generate the unidirectional action potentials to produce collision blocks with respect to the body-generated action potentials propagated through the small-diameter fibers.

Preferably, this aspect of the invention utilizes the tripolar electrode devices described, for example, in the above-cited publications, except that, instead of using such tripolar electrodes for producing collision blocks of action potentials travelling through motor nerves away from the central nervous system in order to control muscular or glandular activity, there are used to produce collision blocks of action potentials propagated through sensory nerves towards the central nervous system in order to reduce pain sensations without unduly hindering other sensations.

According to another aspect of the present invention, there is provided a method of selectively suppressing the propagation of of body-generated action potentials propagated in a predetermined direction at a first velocity through a first group of nerve fibers in a nerve bundle without unduly suppressing the propagation of body-generated action potentials propagated in the predetermined direction at a different velocity through a second group of nerve fibers in the nerve bundle, comprising: applying a plurality of electrode devices to, and spaced along the length of, the nerve bundle, each electrode device beams capable of outputting, when actuated, unidirectional electrode-generated action potentials producing collision blocks with respect to the body-generated action potentials propagated through the second type of nerve fibers; and sequentially actuating the electrode devices with delays timed to the first velocity to produce a "green wave" of anodal blocks minimizing undesired blocking of the body-generated action potentials propagated through the first group of nerve fibers while maximizing the generation rate of said unidirectional electrode-generated action potentials producing collision blocks with respect to the body-generated action potentials propagated through said second type of nerve fibers.

Such a method may be used for producing collision blocks in sensory nerve fibers in order to suppress pain, and also in motor nerve fibers to suppress selected muscular or glandular activities.

According to a further aspect of the invention, there is provided a method of selectively controlling nerve fibers in a nerve bundle having fibers of different diameters propagating action potentials at velocities corresponding to their respective diameters, comprising: applying a plurality of electrode devices to, and spaced along the length of, the nerve bundle, each electrode device being capable of producing, when actuated, unidirectional electrode-generated action potentials; and sequentially actuating the electrode devices with delays timed to the velocity of propagation of action potentials through the fibers of one of the diameters.

In some described preferred embodiments, the electrode devices are sequentially actuated to generate unidirectional action potentials producing collision blocks of the body-generated action potentials propagated through the nerve fibers of another diameter. Such collision blocks may be used for suppressing pain sensations without unduly interfering with normal sensations, or for selectively suppressing certain motor controls without unduly interfering with others.

According to still further aspects of the present invention, there is provided apparatus for use in the above methods.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

The Tripolar Electrode

A basic element in the preferred embodiments of the method and apparatus described below is the tripolar electrode device. Its construction and operation are diagrammatically illustrated in FIG. 1.

Figure 1:
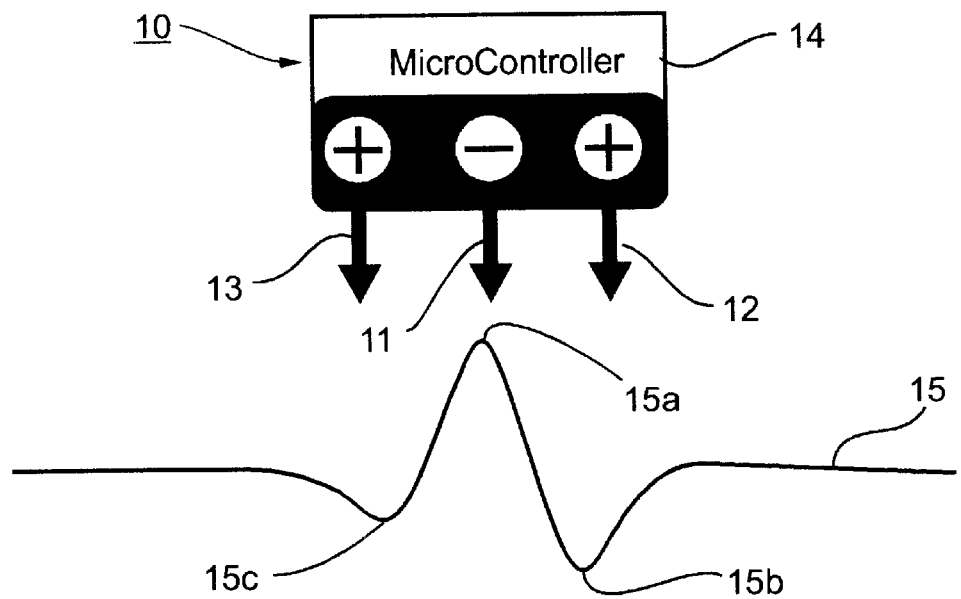
FIG. 1 illustrates the construction and mode of operation of a tripolar electrode device particularly useful in the present invention.

As shown in FIG. 1, the tripolar electrode device, therein designated 10, includes three electrodes, namely, a central cathode 11, a first anode 12 on one side of the cathode, and a second anode 13 on the opposite side of the cathode. The illustrated tripolar electrode device further includes a microcontroller 14 for controlling the three electrodes 11, 12 and 13, as will be described below.

Curve 15 shown in FIG. 1 illustrates the activation function performed by the tripolar electrode device 10 on the nerve bundle underlying it. As shown in FIG. 1, this activation function includes a sharp positive peak 15a underlying the cathode 11, a relatively deep negative dip 15b underlying the anode 12, and a shallower negative dip 15c underlying the anode 13.

When the tripolar electrode 10 is placed with its cathode 11 and anodes 12, 13 in contact with, or closely adjacent to, a nerve bundle, the energization of the cathode 11 generates, by cathodic stimulation, action potentials in the nerve bundle which are propagated in both directions; the energization of anode 12 produces a complete anodal block to the propagation of the so-generated action potentials in one direction; and the energization of anode 13 produces a selective anodal block to the propagation of the action potentials in the opposite direction.

It is known that large-diameter nerve fibers have low excitation thresholds and higher conduction velocities than progressively smaller-diameter nerve fibers; and therefore the tripolar electrode device can generate unidirectional action potentials in the small-diameter fibers while blocking in the large-diameter fibers. It is also known that changing the ratio of the anodal currents can produce gradual recruitment of the large fibers; see for example the above-cited Fitzpatrick et al and Bratta et al publications, incorporated herein by reference. However, whereas this technique is described in the above-cited publications for producing collision blocks of action potentials propagated from the central nervous system via motor fibers in order to stimulate or suppress muscular or glandular activity, in the present invention, according to one aspect, this technique is used for pain control by blocking pain sensations propagated towards the central nervous system in small-diameter sensory fibers without unduly hindering normal sensations propagated through the large-diameter sensory fibers.

According to another aspect of the present invention, a plurality of electrode devices, preferably of such tripolar electrodes, are used to generate a sequence of electrode-generated action potentials (EGAPs) for more effectively suppressing the propagation of body-generated action potentials (BGAPs) propagated through sensory nerves towards the central nervous system (CNS) for pain control, as well as for suppressing the propagation of body-generated action potentials propagated through motor nerves from the central nervous system towards the peripheral nervous system (PNS) for muscular or glandular stimulation or suppression. As will be described more particularly below, the plurality of electrode devices are sequentially actuated with delays to produce a "green wave" of unidirectional EGAPs effective to reduce the interference with the BGAPs propagated unhindered, or to reinforce the stimulation of muscular or glandular activities desired to be effected.

The Overall Apparatus

Figure 2:
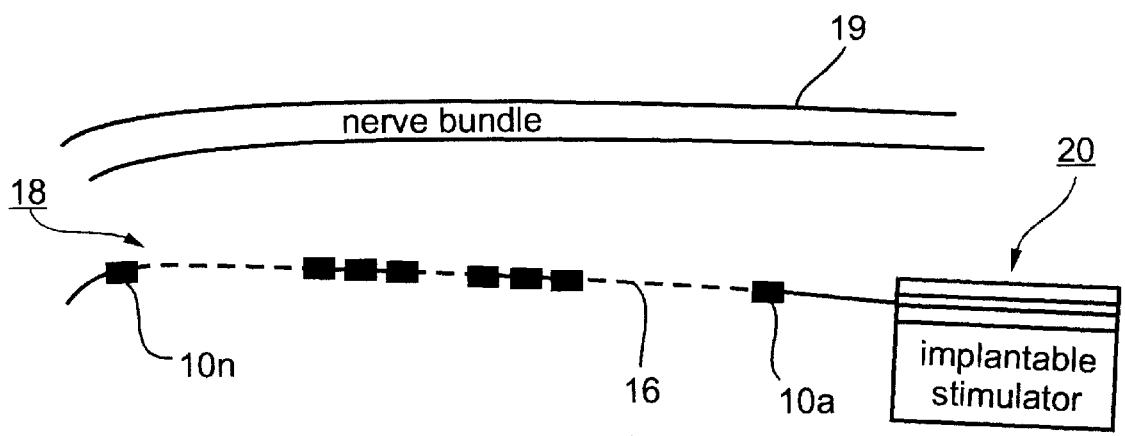
FIG. 2 diagrammatically illustrates an array of tripolar electrode devices constructed in accordance with the present invention for selectively blocking the propagation through certain nerve-fibers of body-generated action potentials.
Figure 3:
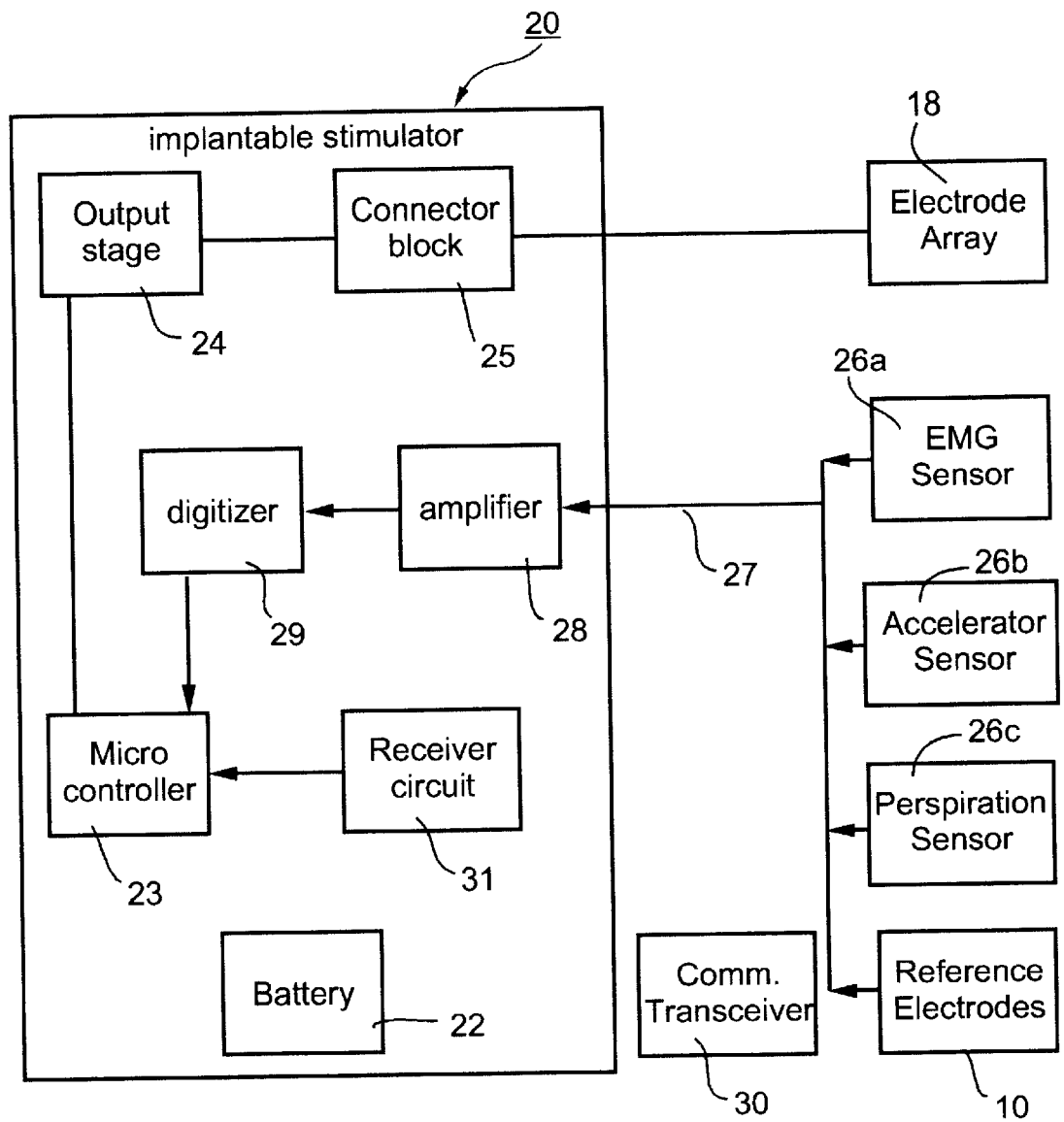
FIG. 3 is a block diagram illustrating the stimulator in the apparatus of FIG. 2.

FIGS. 2 and 3 are diagrams illustrating one form of apparatus constructed in accordance with the present invention utilizing a plurality of the tripolar electrode devices, therein designated 10a–10n, shown in FIG. 1. Such electrode devices are interconnected by a bus 16 to form an electrode array 18 to be applied, as by implantation, with the electrode devices spaced along the length of the nerve bundle, shown at 19, and to be selectively actuated, as will be described more particularly below, by a stimulator, generally designated 20. The construction of the stimulator 20 is more particularly illustrated in FIG. 3.

Each of the electrode devices 10a–10n is of the tripolar construction shown in FIG. 1, to include a central cathode 11 flanked on its opposite sides by two anodes 12, 13. Each such electrode device further includes a microcontroller, shown at 14 in FIG. 1, and more particularly described below with respect to FIG. 7, for sequentially controlling the actuation of the electrodes 11–13 of each electrode device in order to produce the "green wave" briefly described above, and to be more particularly described below.

The assembly of electrode devices 10a–10n, and the stimulator 20 for sequentially actuating them, are preferably both implantable in the body of the subject with the electrodes in contact with, or closely adjacent to, the nerve bundle 15. Accordingly, the simulator 20 includes its own power supply, shown at 22 in FIG. 3. The stimulator 20 further includes a microcontroller 23 having output stage 24 connected, via connector block 25, to the plurality of electrode devices 10a–10n for sequentially actuating them, as will be described below.

Stimulator 20 further includes an input circuit for inputting various sensor signals for purposes of calibration and/or control. As shown in FIG. 3, such inputs may be from an EMG (electromyogram) signal sensor 26a and from an accelerator sensor 26b. The EMG sensor 26a may be used for calibration purposes, e.g., to calibrate the apparatus according to EMG signals generated by a subject's muscle during the calibration of the apparatus (described below), or for control purposes, e.g., for automatically actuating the device upon the occurrence of a particular EMG signal. The accelerator sensor 26b may be used for control purposes, e.g., to automatically actuate the device upon the occurrence of tremors or spasms in order to suppress in the tremors by blocking certain motor nerves.

Stimulator 20 may also have an input from a perspiration sensor 26c for automatic control of sweat glands. It may also have an input from one of the electrodes serving as a reference electrode for calibration purposes, as will also be described more particularly below.

The inputs into the stimulator 20 may be by wire or bus, as shown at 27 in FIG. 3. Such inputs are amplified in amplifier 28, and digitized in a digitizer 29, before being inputted into the microcontroller 23.

The inputs to the stimulator 20 may also be by wireless communication, as schematically shown at 30 in FIG. 3, particularly where the device is implanted. For this purpose, stimulator 20 includes a receiver 31 for receiving such inputs. Such inputs are also amplified in amplifier 28 and digitized in digitizer 29 before being inputted into the microcontroller 23.

Operation of the Illustrated Apparatus

The apparatus illustrated in FIGS. 2 and 3, when applied along the length of the nerve bundle 15 as shown in FIG. 2, is capable of suppressing the propagation of body-generated action potentials (BGAPs) propagated through the small-diameter nerve fibers in a nerve bundle without unduly suppressing the propagation of BGAPs propagated through the large-diameter nerve fibers in the nerve bundle. One application of such a device is to reduce pain sensations; and another application of the device is to suppress muscular or glandular activities. The apparatus illustrated in FIGS. 2 and 3 may also be used for generating, by the electrode devices, action potentials (hereinafter frequently referred to as electrode-generated action potentials, or EGAPS) where the body fails to produce the necessary BGAPs to produce a particular muscular or glandular activity. A further application of the apparatus, therefore, is to stimulate a muscular or glandular activity.

As described above, when the cathode 11 of each tripolar electrode device 10 is actuated, it generates an action potential by cathodic stimulation propagated in both directions; whereas when anode 12 of the respective tripolar electrode 10 is energized, it produces a complete anodal block on one side of the cathode, to thereby make the electrode-generated action potential unidirectional and propagated away from the central nervous system. On the other hand, when anode 13 is energized, it produces an anodal block only with respect to the BGAPs propagated through the large-diameter sensory nerves, since they are more sensitive to the anodal current. Accordingly, the EGAPs from the small-diameter sensory nerves are permitted, to a larger extent, to propagate through the anodal block.

The EGAPs outputted by the anodal block may be used as collision blocks with respect to sensory BGAPs to suppress pain, or with respect to motor BGAPs to suppress undesired muscular activity (e.g., tremors, spasms), or glandular activity (e.g., excessive perspiration).

An undesired side effect of this activation scheme, is that at the time when anode 12 of device 10 is actuated to generate an anodal block as described above, all BGAPs in both small and large fibers are blocked and cannot pass the device. Thus every production of an EGAP is accompanied by a brief period in which all BGAPs cannot pass the site of the device 10. In order to minimize the blocking of BGAPs while maximizing the amount of EGAPs produced, the tripolar electrode devices 10a–10n are sequentially actuated, under the control of the stimulator 20. This sequential actuation is timed with the propagation velocity of the action potentials through the nerve fiber not to be blocked. Thus, as well known for controlling vehicular traffic, when stop lights spaced along a thoroughfare are controlled to define a "green wave" travelling at a predetermined velocity, the vehicles travelling at the "green wave" velocity will be less hindered than if the stop lights were not synchronized with their velocity.

The anodal blocks produced by the sequential actuation of the tripolar electrodes are comparable to the stop lights in a thoroughfare, and therefore the action potentials travelling at the velocity of the green wave will be less hindered by such stop lights or anodal blocks.

Thus, where the invention is used for pain control by suppressing the BGAPs in the small-diameter sensory nerves, producing a "green wave" of anodal blocks timed with the conduction velocity through the large-diameter sensory nerves, there will be less interference with the BGAPs representing normal sensations, travelling through the large-diameter sensory nerve fibers, as compared to the BGAPs representing pain sensations travelling through the small-diameter sensory nerve fibers which will be collision blocked by the EGAPs.

The same "green wave" effect can be provided in order to suppress BGAPs propagating through motor nerve fibers in order to block motor controls of selected muscles or glands.

Examples of Use of the Apparatus

Figure 4:
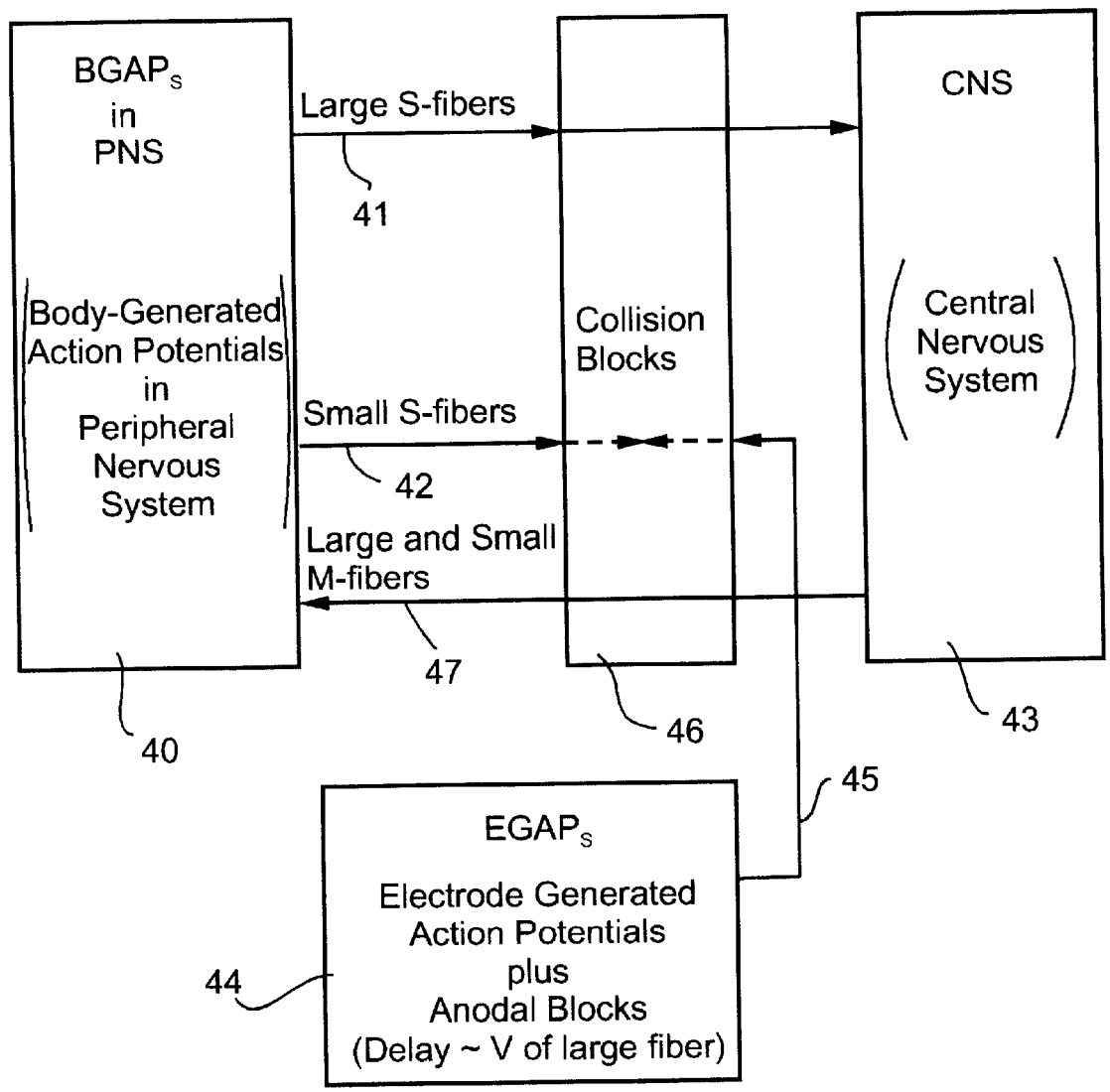
FIG. 4 is a block diagram illustrating the operation of the apparatus of FIGS. 2 and 3 for suppressing pain sensations.

FIG. 4 illustrates an example of use of the described apparatus for reducing pain sensations by suppressing the BGAPs transmitted through the small-diameter sensory fibers without unduly hindering the transmission of the BGAPs through the large-diameter sensory fibers.

Thus, as shown in FIG. 4, the BGAPs in the peripheral nervous system PNS (block 40) generate normal sensations in the large sensory fibers 41 and pain sensations in the small sensory fibers 42. Normally, both types of sensations are propagated through their respective fibers to the central nervous system (CNS, block 43).

However, as shown in FIG. 4, the assembly of electrodes 10a–10n, when sequentially actuated with delays timed to the conduction velocity of the large-diameter fibers 41, generates unidirectional EGAPs (block 44) which are outputted with delays timed to correspond to the velocity of the large sensory fibers (as shown at 45) to produce a collision block (46) with respect to the BGAPs propagated through the small sensory fibers (42) without unduly hindering the BGAPs propagated through the large sensory fibers 41 to the central nervous system 43. Accordingly, the pain sensations normally propagated through the small sensory fibers 42 to the central nervous system 43 will be suppressed, while the normal sensations propagated through the large sensory fibers 41 will continue substantially unhindered to the central nervous system.

In addition, as shown by line 47 in FIG. 4, the motor action potentials from the CNS to the PNS are also substantially unhindered.

Figure 5A:
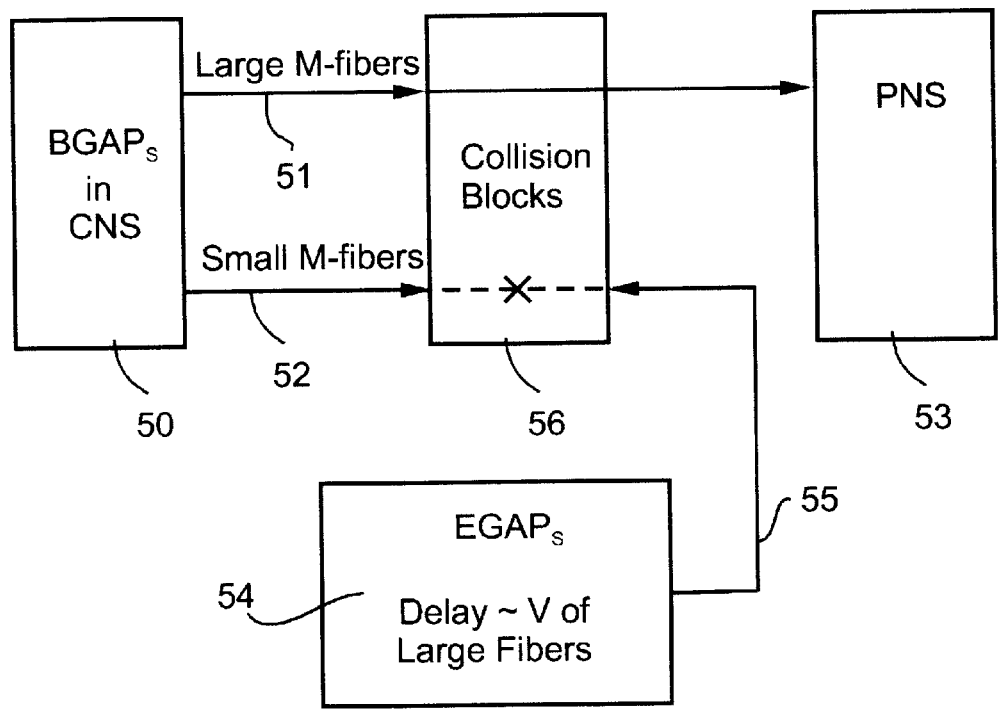
FIGS. 5a and 5b are block diagrams illustrating how the apparatus of FIGS. 2 and 3 may also be used for suppressing selected muscular or glandular activities controlled by the motor nerves.
Figure 5B:
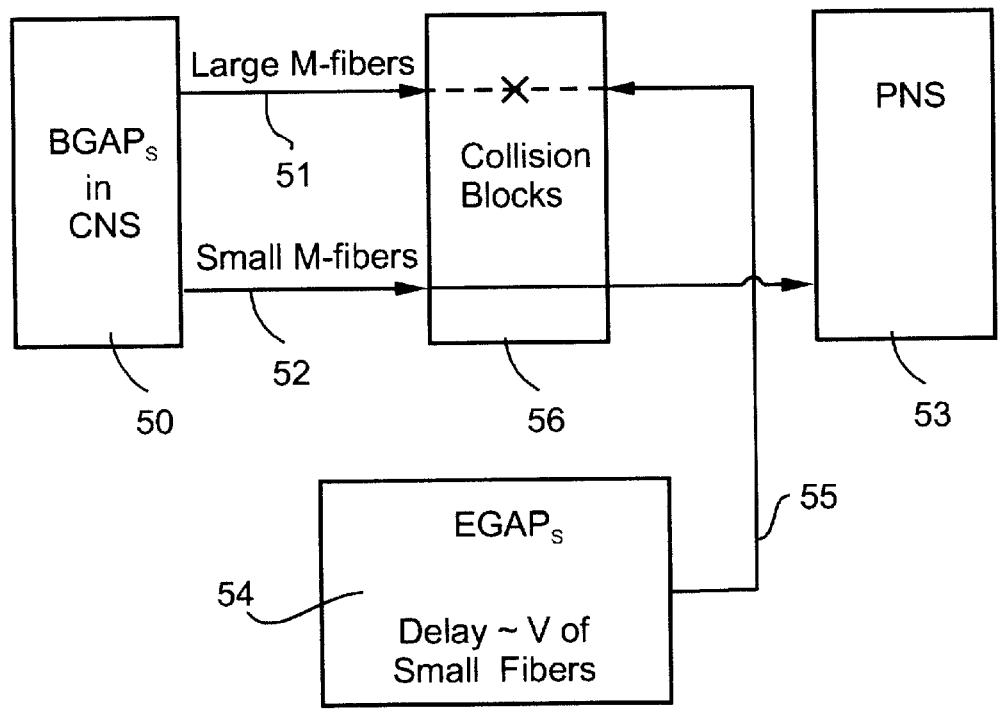

FIGS. 5a and 5b illustrate the application of the apparatus for suppressing certain muscular or glandular activities normally controlled by the BGAPs transmitted through the motor nerve fibers. In this case, as shown in FIG. 5a, the BGAPs are generated in the central nervous system (block 50) and are normally transmitted via large motor fibers 51 and small motor fibers 52 to the peripheral nervous system 53. FIG. 5a illustrates the arrangement wherein the EGAPs are generated at a rate corresponding to the velocity of the large motor fibers, as shown by blocks 54 and 55, so that they produce collision blocks with respect to the small motor fibers 52, and permit the BGAPs to be transmitted through the large motor fibers 51 to the peripheral nervous system 53.

FIG. 5b illustrates the variation wherein the apparatus generates EGAPs at a rate corresponding to the velocity of the small motor fibers (blocks 54, 55), such that the collision blocks (56) block the large motor fibers 51, and permit the BGAPs to be transmitted to the peripheral nervous system 53.

Figure 6A:
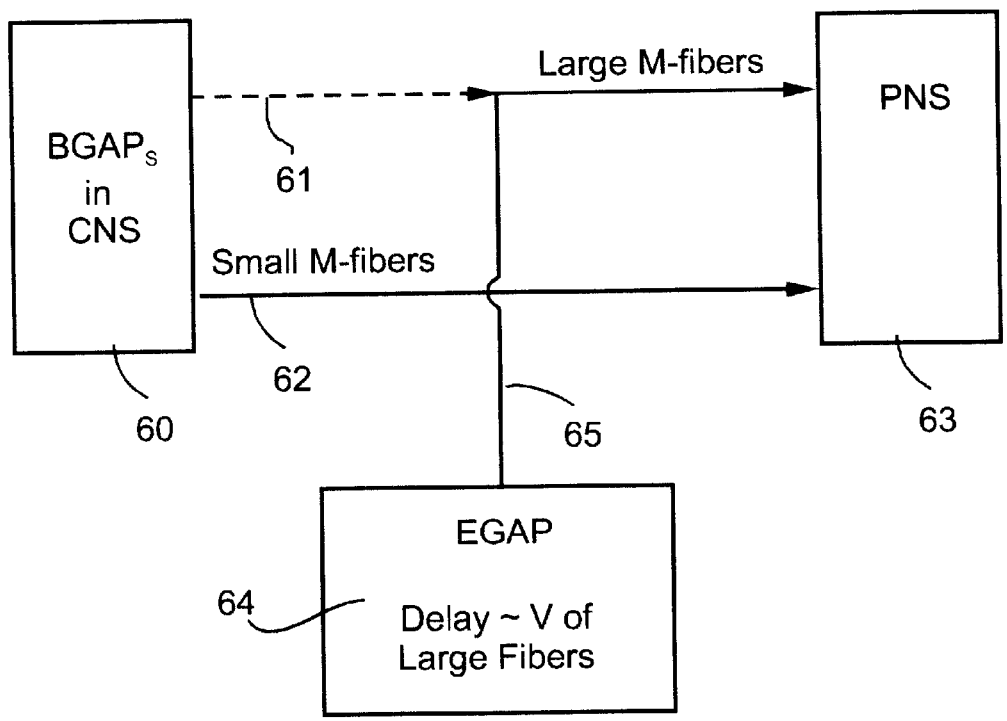
FIGS. 6a and 6b are block diagrams illustrating how the apparatus of FIGS. 2 and 3 may also be used for stimulating selected motor or glandular activities upon the failure of the body to generate the required action potentials.
Figure 6B:
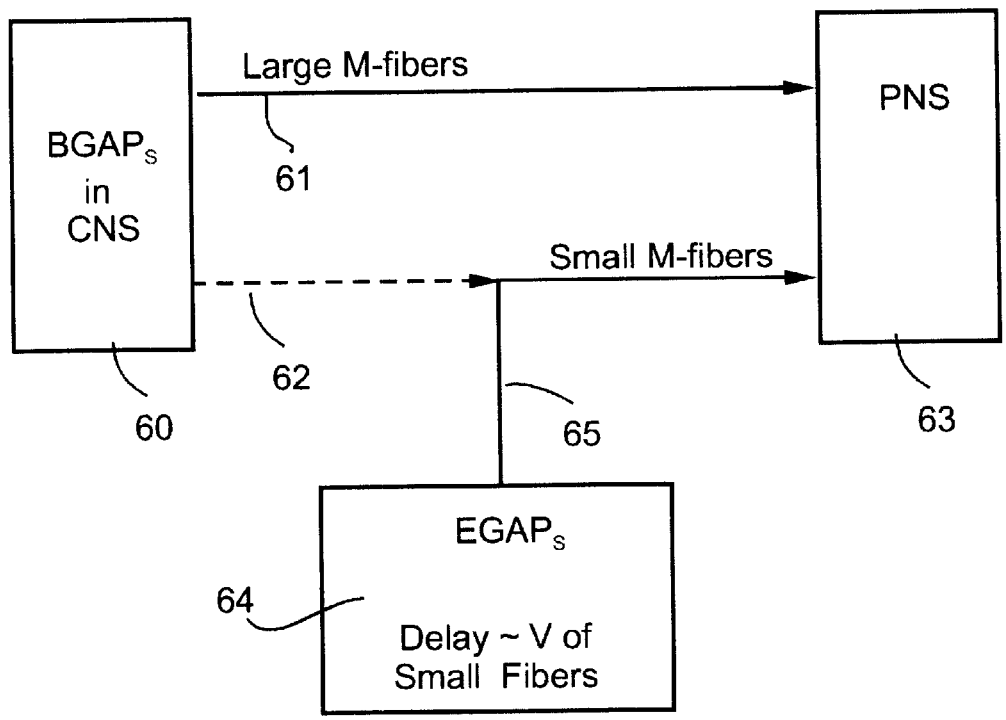

FIGS. 6a and 6b illustrate the applications of the apparatus for stimulating a particular muscle or gland where the body fails to develop adequate BGAPs in the respective motor nerve fiber for the respective muscular or glandular control. In this case, the apparatus generates unidirectional EGAPs selectively for the respective muscle or gland.

FIG. 6a illustrates the application of the invention wherein the body fails to generate in the central nervous system 60 adequate BGAPs for transmission by the large motor fibers to the peripheral nervous system 63, in which case the electrode devices 10a–10n in the electrode assembly would be sequentially energized by the stimulator 64 with delays timed to the velocity of propagation of action potentials through the large motor fibers. The unidirectional EGAPs are thus produced with delays timed to the conductive velocity of the large motor fibers, thereby permitting them to be transmitted via the large motor fibers to the peripheral nervous system.

FIG. 6b, on the other hand, illustrates the case where the electrodes 10a–10n are sequentially energized with delays timed to the velocity of the small motor fibers, thereby permitting the unidirectional EGAPs to be outputted via the small-diameter fibers to the peripheral nervous system 63.

Calibration

For best results, each electrode assembly should be calibrated for each patient and at frequent intervals. Each calibration requires adjustment of the cathodic and anodic currents in each tripolar electrode, and also adjustment of the timing of the sequential actuation of the tripolar electrodes.

To calibrate the cathodic and anodic currents for each electrode, the proximal electrode (10a, FIG. 2) is actuated to produce a unidirectional action potential propagated towards the distal electrode (10n) at the opposite end of the array. The so-produced action potential, after having traversed all the electrodes between electrodes 10a, and 10n, is detected and recorded by the distal electrode 10n. The currents in the electrodes are iteratively adjusted to produce maximum blocking.

Figure 7A:
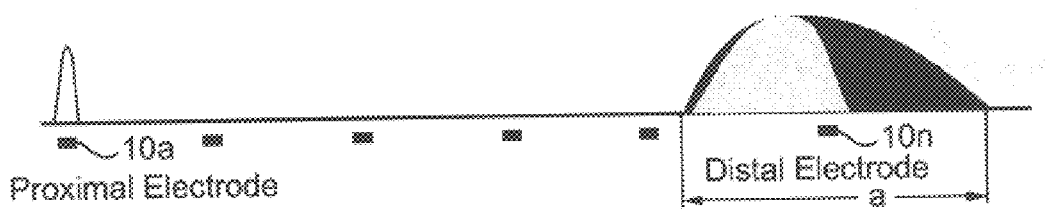
FIGS. 7a and 7b are diagrams helpful in explaining the manner of calibrating the apparatus of FIGS. 2 and 3.

FIG. 7a illustrates, at "a", the signal detected by the distal electrode when the blocking is minimum, and at "b" when the signal detected by the distal electrode when the blocking is maximum.

Figure 7B:
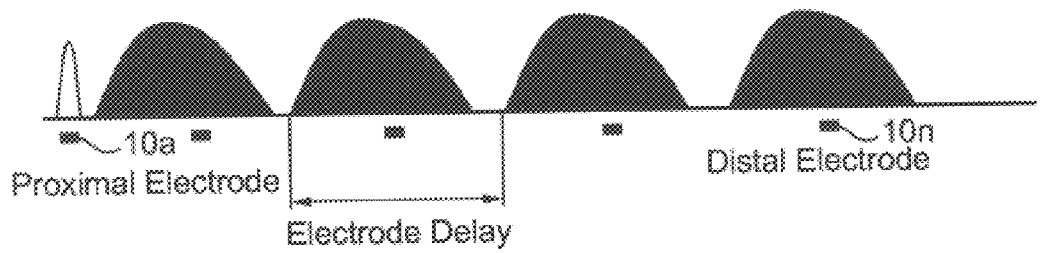

FIG. 7b illustrates the manner of calibrating the electrode array to produce the proper timing in the sequential actuation of the electrodes for calibrating the sequential timing, the proximate electrode (10a) is again actuated to produce a unidirectional action potential propagated toward the distal electrode (10n). As the so-produced action potential traverses all the electrodes inbetween, each such inbetween electrode detects and records the action. This technique thus enables calibrating the electrode array to produce the exact delay between the actuations of adjacent electrodes to time the sequential actuations with the conduction velocity of the respective nerve fiber.

For example, where the sequential actuation is to produce a "green wave" having a velocity corresponding to the conduction velocity of the large sensory nerve fibers for reducing pain sensations, the timing would be adjusted so as to produce the sequential delay shown in FIG. 7b to thereby time the sequential actuations of the electrodes to the conductive velocity in the large sensory fibers.

The EMG sensor 26a shown in FIG. 3 may also be used for calibrating the electrode currents and sequential timing when the apparatus is to be used for providing a stimulation of a muscular or glandular activity where the body fails to provide the necessary BGAPs for this purpose. In this case, the currents and timing would be adjusted to produce a maximum output signal from the EMG sensor 26a for the respective muscle.

The EMG sensor 26a could also be used to automatically actuate the apparatus upon the detection of an undesired EMG signal, e.g., as a result of a tremor or spasm to be suppressed. For example, the accelerator sensor 26b could be attached to a limb of the subject so as to automatically actuate the apparatus in order to suppress tremors in the limb upon detection by the accelerator.

Other sensors could be included, such as an excessive perspiration sensor 26c, FIG. 3. This would also automatically actuate the apparatus to suppress the activity of the sweat glands upon the detection of excessive perspiration.

A Preferred Electrode Array Construction

Figure 8:
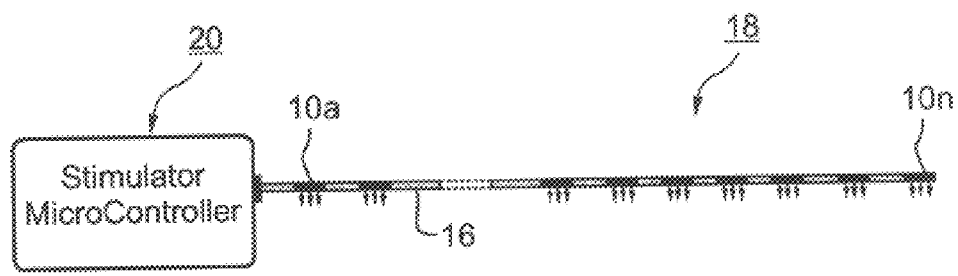
FIG. 8 illustrates one form of assembly of a plurality of tripolar electrode devices constructed in accordance with the present invention for use in the apparatus of FIGS. 2 and 3.
Figure 9:
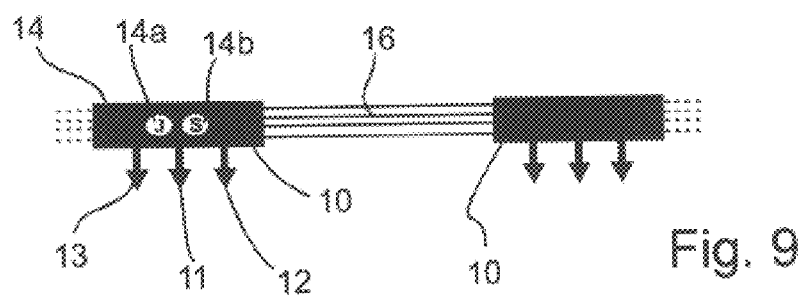
FIG. 9 diagrammatically illustrates the manner of controlling the electrode devices in the assembly of FIG. 5 by means of an asynchronous serial four-wire bus.

FIGS. 8 and 9 illustrate a preferred construction for the electrode array 18, including the plurality of tripolar electrode devices 10a–10n interconnected by bus 16 and connected to the stimulator 20. In this preferred construction, as shown in FIG. 9, the bus 16 interconnecting the tripolar electrodes 10a–10n is an asynchronous serial four-wire bus. Such an arrangement may use the well-known JTAG/IEEE 1149.1 Protocol, in which a four-wire bus (as shown at Vcc, TX, RX and GND, FIG. 10) carries the data to all the electrode devices connected in serial. In such case, the microcontroller circuitry (14, FIG. 1) in each tripolar electrode device 10 would include a JTAG controller 14a acting as a communication processor, and a stimulation processor 14b. The communication processor 14a processes the commands issued by the stimulator microcontroller 20 and passes any relevant commands to the stimulation processor 14b of the respective tripolar electrode device. This enables two-way communication between the stimulator controller and each tripolar electrode device utilizing only four wires.

Instead of using the JTAG/IEEE 1149.1 Protocol or other asynchronous four wires bus wireless communication may also be used by using an established wireless protocol, e.g., Bluetooth. Wireless communication can be advantageous if the stimulator microcontroller 20 is separated from the electrode array 18 in order to avoid the possibility of mechanical breakage of long electrode leads.

A Preferred Tripolar Electrode Construction

Figure 10:
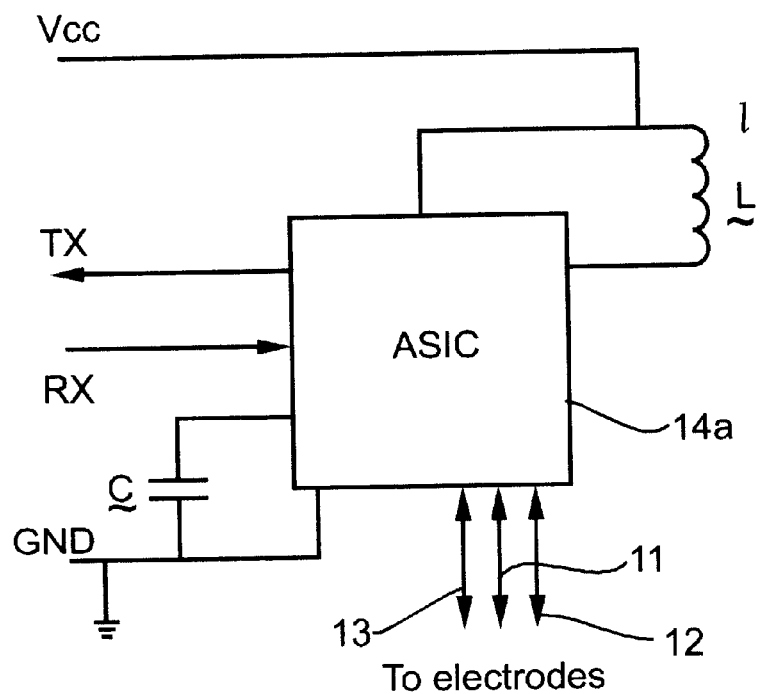
FIG. 10 is an electrical diagram schematically illustrating the construction of one of the tripolar electrode devices used in the assembly of FIGS. 8 and 9.
Figure 11A:
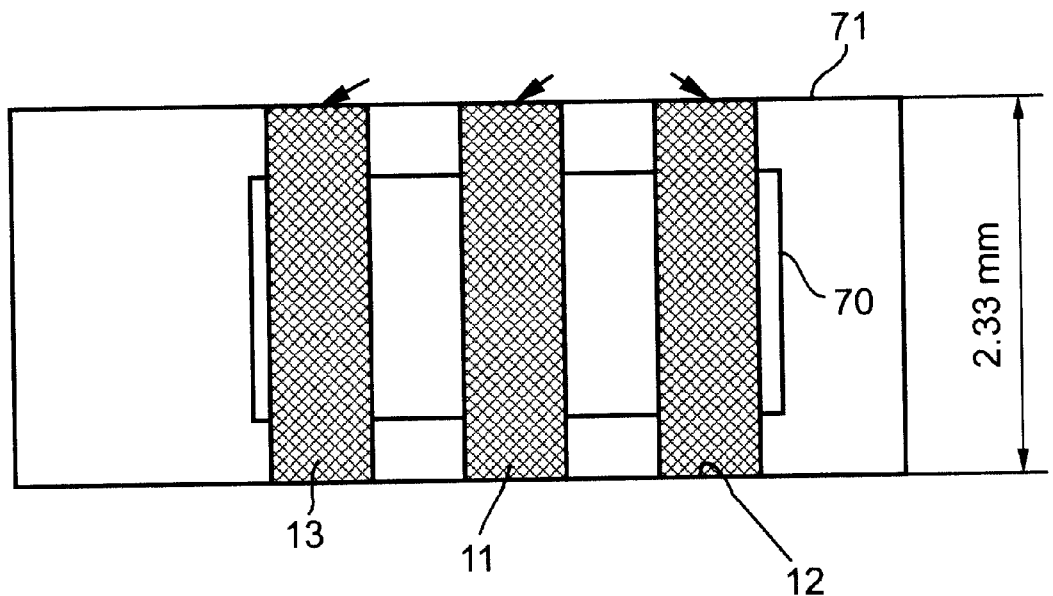
FIGS. 11a, 11b and 11c are side, plan and end views, respectively, diagrammatically illustrating the construction of one of the tripolar electrode devices used in the electrode assembly of FIGS. 8 and 9.
Figure 11B:
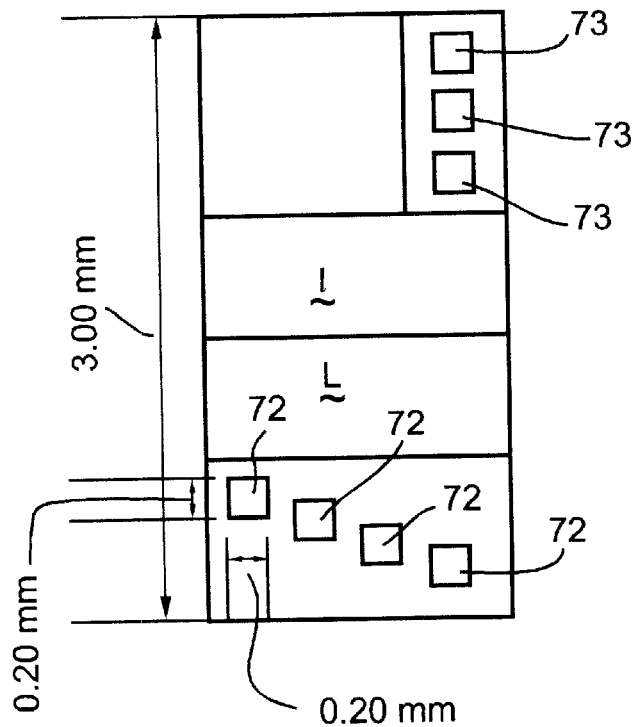
Figure 11C:
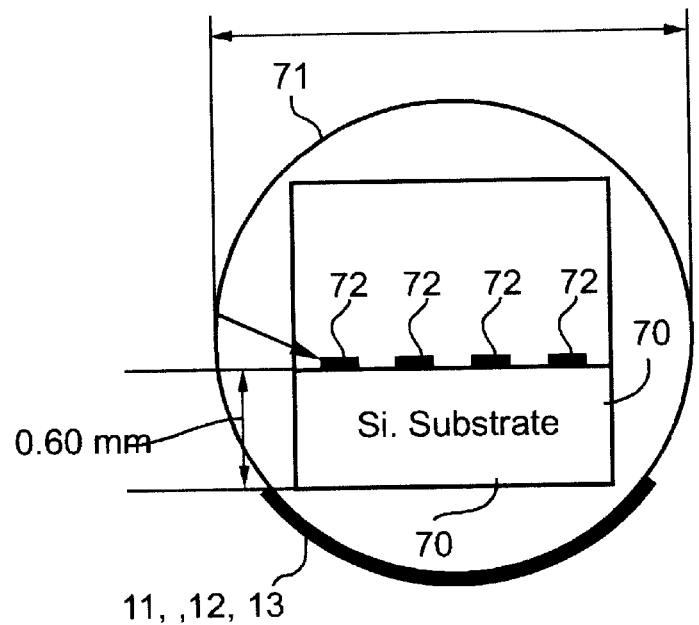

FIG. 10 diagrammatically illustrates a preferred electrical construction, and FIGS. 11a–11c diagrammatically illustrate a preferred physical construction, for each of the tripolar electrodes 10 included in the electrode array 18 of FIG. 2.

Thus, FIG. 10 illustrates the four-wire connections to the communication processor 14a briefly described above. As also seen in FIG. 10, each tripolar electrode further includes a capacitor C (e.g., at least 10 μF, preferably 20 μF), and a coil L (e.g., at least 50 μH, preferably 68 μH) connected to the communication processor and defining a pulsing circuit for pulsing the electrodes 11, 12, 13 controlled by the communication processor.

The physical construction of each of the tripolar electrode devices is shown by the diagrammatic side view 11a, plan view 11b, and end view 11c.

Thus, as shown in these views, each tripolar electrode device includes a to silicon substrate 70 within a sleeve 71 formed with the three electrodes 11, 12, 13 as longitudinally-spaced conductive strips on one face to be brought into direct contact, or very close proximity, to the nerve bundle. The silicon substrate 70 carries the electrical circuitry (14, FIG. 1) including the microcontroller 14a, the capacitor C, and coil L of the respective pulsing network. The silicon substrate 70 further includes conductive deposits (e.g., nickel) 72 for connection to the four wires of the bus (as shown in FIG. 10), and further conductive deposits (e.g., nickel) 73 for connection to the three electrodes 11, 12, 13.

An example of the various dimensions in the construction of each tripolar electrode is shown in FIGS. 11a–11c.

Example of Use of the Apparatus

Figure 12:
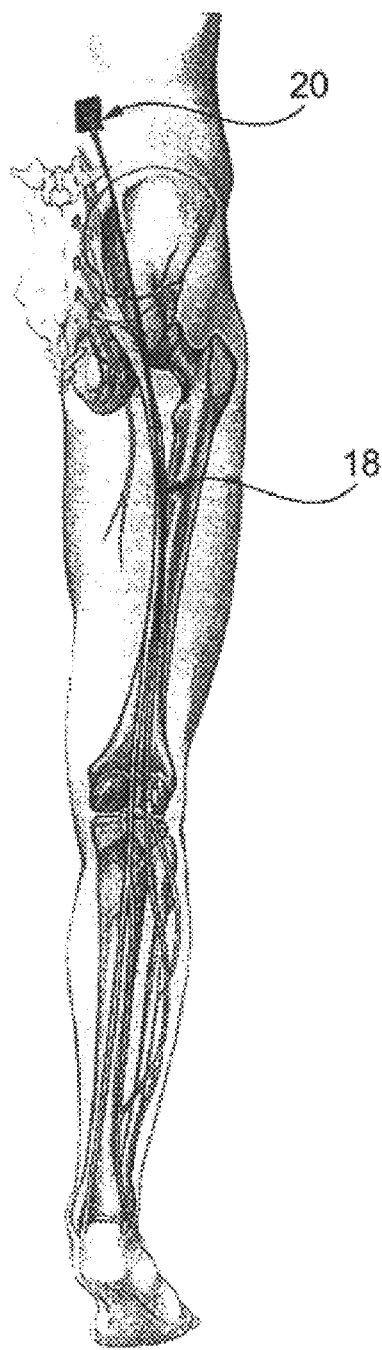
FIG. 12 illustrates the electrode assembly of FIGS. 8 and 9 applied for blocking the propagation of body-generated action potentials in the sciatic nerve fiber in the leg of a subject.

FIG. 12 illustrates the apparatus as including one electrode array 18 powered by one stimulator 20 both implanted in the leg of a subject for suppressing pain originating from the sciatic nerve.

Figure 13:
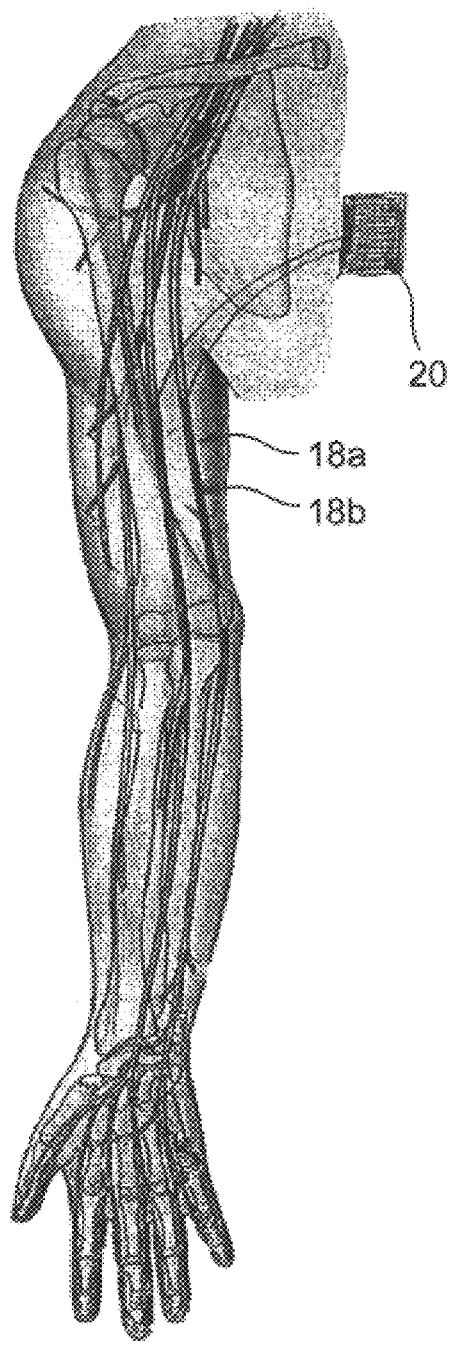
FIG. 13 illustrates the electrode assembly of FIGS. 8 and 9 applied for blocking the propagation of body-generated action potentials through two nerve fibers in the arm of a subject.

FIG. 13 illustrates two electrode arrays, shown as 18a, 18b, implanted in the arm of the subject and both powered by a common stimulator 20 also implanted in the subject.

While FIGS. 12 and 13 illustrate the apparatus as implanted in the body of the subject, in some applications it may be preferable to apply the apparatus externally of the subject's body and make connections from the electrodes to the respective nerve bundle.

Accordingly, while the invention has been described with respect to several preferred embodiments, it will be appreciated that these are set forth merely for purposes of example, and that many other variations, modifications and applications of the invention may be made.

What is claimed is:

1. A method of reducing pain sensations resulting from the propagation of body-generated action potentials towards the central nervous system through small-diameter sensory fibers in a nerve bundle, without unduly reducing other sensations resulting from the propagation of body-generated action potentials towards the central nervous system through large-diameter sensory fibers in said nerve bundle, comprising:

applying to said nerve bundle at least one electrode device capable, upon actuation, of generating unidirectional action potentials to be propagated through both the small-diameter and large-diameter sensory fibers in said nerve bundle away from said central nervous system; and actuating said electrode device to generate said unidirectional action potentials to produce collision blocks with respect to said body-generated action potentials propagated through said small-diameter fibers.

2. The method according to claim 1, wherein said electrode device includes electrodes which:

(a) generate said electrode-generated action potentials by cathodic stimulation;

(b) produce a complete anodal block on one side of the cathode to make said electrode-generated action potentials unidirectional; and (c) produce a selective anodal block on the opposite side of the cathode to cause the electrode-generated action potentials to produce collision blocks with respect to the body-generated action potentials propagated through the small-diameter sensory fibers.

3. The method according to claim 2, wherein said electrode device is a tripolar electrode device which includes a central cathode for producing said cathodic stimulation, a first anode on one side of the cathode for producing said complete anodal block, and a second anode on the opposite side of said cathode for producing said selective anodal block.

4. The method according to claim 1, wherein there are a plurality of said electrode devices spaced along the length of the nerve bundle; and wherein said electrode devices are sequentially actuated with delays timed to the velocity of propagation of the body-generated action potentials through said large-diameter fibers to produce a "green wave" of electrode-generated anodal blocks, thereby increasing the number of EGAPs in the small diameter fibers producing collision blocks while minimizing anodal blocking of the BGAPs propagated through the large-diameter sensory fibers.

5. A method of selectively suppressing the propagation of body-generated action potentials propagated in a predetermined direction at a first velocity through a first group of nerve fibers in a nerve bundle without unduly suppressing the propagation of body-generated action potentials propagated in said predetermined direction at a different velocity through a second group of nerve fibers in said nerve bundle, comprising:

applying a plurality of electrode devices to, and spaced along the length of, the nerve bundle, each electrode device being capable of outputting, when actuated, unidirectional electrode-generated action potentials producing collision blocks with respect to the body-generated action potentials propagated through said second type of nerve fibers;

and sequentially actuating said electrode devices with delays timed to said first velocity to produce a "green wave" of anodal blocks minimizing undesired blocking of said body-generated action potentials propagated through said first group of nerve fibers, while maximizing the generation rate of said unidirectional electrode-generated action potentials producing collision blocks with respect to the body-generated action potentials propagated through said second type of nerve fibers.

6. The method according to claim 5, wherein said first group of nerve fibers are large-diameter nerve fibers; and said second group of nerve fibers are small-diameter nerve fibers.

7. The method according to claim 6, wherein said nerve fibers are sensory nerve fibers, in which said predetermined direction of propagation of the body-generated action potentials to be collision blocked is towards the central nervous system, said method being effective for suppressing pain sensations propagated through the small-diameter sensory fibers without unduly suppressing other sensations propagated through the large-diameter sensory fibers.

8. The method according to claim 6, wherein said nerve fibers are motor nerve fibers in which said predetermined direction of propagation of the body-generated action potentials to be collision blocked is away from the central nervous system towards a muscle or gland, said method being effective for suppressing motor impulses propagated through the small-diameter motor nerve fibers without unduly suppressing the propagation of the motor impulses through the large-diameter motor nerve fibers.

9. The method according to claim 5, wherein each of said electrode devices is a tripolar electrode which includes a central cathode for producing said electrode-generated action potentials by cathodic stimulation, a first anode on one side of the cathode for making said electrode-generated action potentials unidirectional, and a second anode on the opposite side of said cathode for producing a selective anodal blocking of said electrode-generated action potentials.

10. A method of selectively controlling nerve fibers in a nerve bundle having fibers of different diameters propagating action potentials at velocities corresponding to their respective diameters, comprising:
applying a plurality of electrode devices to, and spaced along the length of, the nerve bundle, each electrode device being capable of producing, when actuated, unidirectional electrode-generated action potentials;
and sequentially actuating said electrode devices with delays timed to the velocity of propagation of action potentials through the fibers of one of said diameters.

11. The method according to claim 10, wherein said electrode devices are sequentially actuated to generate unidirectional action potentials producing collision blocks of the body-generated action potentials propagated through said nerve fibers of a another diameter.

12. The method according to claim 11, wherein said electrode devices are sequentially actuated with delays timed to the velocity of the larger-diameter nerve fibers to produce a "green-wave" of anodal blocks in order to minimize blocking the body-generated action potentials propagated through the larger-diameter fibers while maximizing the number of EGAPs collision blocking the body-generated action potentials propagated through the small diameter fibers.

13. The method according to claim 12, wherein said fibers include large-diameter sensory fibers propagating body-generated action potentials representing normal sensations from the peripheral nervous system to the sensor nervous system, and small-diameter sensory fibers propagating body-generated action potentials representing pain sensations from the peripheral nervous system to the central nervous system, which pain sensations in the small-diameter sensory fibers are suppressed by collision block and said "green-wave" of anodal blocks minimizes blocking of said normal sensations in said large-diameter sensory nerves.

14. The method according to claim 12, wherein said nerve fibers include large-diameter motor fibers propagating body-generated action potentials representing certain motor controls from the central nervous system to the peripheral nervous system, and small-diameter motor nerve fibers representing other motor controls from the central nervous system to the peripheral nervous system, the motor controls in said small-diameter motor fibers being suppressed by collision blocks and said green-wave of anodal blocks minimizes blocking of the motor controls in said large-diameter motor fibers.

15. The method according to claim 10, wherein said nerve fibers are motor fibers of different diameters for propagating body-generated action potentials from the central nervous system to the peripheral nervous system, said electrode devices being sequentially actuated to generate unidirectional action potentials to serve as motor action potentials to be propagated from the central nervous system to the peripheral nervous system to replace motor action potentials failed to be generated by the body.

16. The method according to claim 10, wherein each of said electrode devices is a tripolar electrode which includes a central cathode for producing said electrode-generated action potentials by cathodic stimulation, a first anode on one side of the cathode for making said electrode-generated action potentials unidirectional, and a second anode on the opposite side of said cathode for producing a selective anodal blocking of said electrode-generated action potentials.

17. Apparatus for blocking pain sensations resulting from the propagation of body-generated action potentials towards the central nervous system through a nerve bundle having small-diameter sensory fibers and large-diameter sensory fibers, comprising:
an electrical device adapted to be applied to said nerve bundle and having at least one electrode device capable, upon actuation, of generating unidirectional action potentials to be propagated through both the small-diameter and large-diameter sensory fibers in said nerve bundle away from said central nervous system;
and a stimulator controlled to actuate said electrode device to generate said unidirectional action potentials to produce collision blocks of the body-generated action potentials in said small-diameter sensory fibers such as to selectively block pain sensations resulting from the propagation of body-generated action potentials towards the central nervous system through said small-diameter sensory fibers in the nerve bundle, without unduly reducing other sensations resulting from the propagation of body-generated action potentials towards the central nervous system through said large-diameter sensory fibers in said nerve bundle;
wherein said electrode device includes electrodes which, when actuated by said stimulator:
(i) generate said electrode-generated action potentials by cathodic stimulation;
(ii) produce a complete anodal block on one side of the cathode to make said electrode-generated action potentials unidirectional; and
(iii) produce a selective anodal block on the opposite side of the cathode to block the electrode-generated action potentials propagated through the large-diameter sensory fibers to a greater extent than those propagated through the small-diameter sensory fibers;
wherein said electrode device is a tripolar electrode which includes a central cathode for producing said cathodic stimulation, a first anode on one side of the cathode for producing said complete anodal block, and a second anode on the opposite side of said cathode for producing said selective anodal block; and
wherein there are a plurality of said electrode devices spaced along the length of the nerve bundle; and
wherein said electrode devices are sequentially actuated by said stimulator with delays corresponding to the velocity of propagation of the body-generated action potentials through said large-diameter fibers to produce a "green wave" of electrode-generated action potentials collision blocking with the body-generated action potentials propagated through the small-diameter fibers while minimizing anodal blocking of action potentials propagating through the large-diameter fibers.

18. Apparatus for suppressing the propagation of body-generated action potentials propagated at first and second velocities through first and second types of nerve fibers in a nerve bundle, comprising:
a plurality of electrodes adapted to be spaced along the length of the nerve bundle, each capable of producing, when actuated, unidirectional electrode-generated action potentials and a selective anodal block of the latter action potentials propagated through said first type of nerve fibers to a greater extent than those propagated through said second type of nerve fibers;

and a stimulator for sequentially actuating said electrode devices with delays timed to said first velocity to produce a "green wave" of anodal blocks minimizing undesired blocking of said body-generated action potentials propagated through said first type of nerve fibers, while maximizing the generation rate of said unidirectional electrode-generated action potentials producing collision blocks with respect to the body-generated action potentials propagated through said second type of nerve fibers, such that the apparatus selectively suppresses the propagation of body-generated action potentials propagated at said first velocity through said first type of nerve fibers in the nerve bundle without unduly suppressing the propagation of body-generated action potentials propagated at said second velocity through the second type of nerve fibers in said nerve bundle.

19. The apparatus according to claim 18, wherein each of said electrode devices is a tripolar electrode which includes a central cathode for producing said electrode-generated action potentials by cathodic stimulation, a first anode on one side of the cathode for making said electrode-generated action potentials unidirectional, and a second anode on the opposite side of said cathode for producing said selective anodal blocking of said electrode-generated action potentials, when said tripolar electrode is a actuated by said stimulator.

20. The apparatus according to claim 19, wherein said plurality of electrode devices and said stimulator are constructed to be implanted into the subject's body with the electrodes in contact with or closely adjacent to said nerve bundle.

21. The apparatus according to claim 19, wherein said apparatus further includes an asynchronous, serial four-wire bus, and said stimulator is connected to said plurality of electrode devices by said asynchronous, serial four-wire bus.

22. The apparatus according to claim 19, wherein said apparatus further includes a wireless communication link, and said stimulator communicates with said plurality of electrode devices via said wireless communication link.

23. The apparatus according to claim 19, wherein each of said tripolar electrode devices includes an insulating base carrying said cathode and said first and second anodes on one face thereof, and control circuitry on the opposite face.

24. The apparatus according to claim 23, wherein said control circuitry includes a microprocessor communicating with said stimulator, and an L-C pulsing network controlled by said microprocessor.

25. Apparatus for selectively controlling nerve fibers in a nerve bundle having fibers of different diameters propagating action potentials at velocities corresponding to their respective diameters, comprising:

a plurality of electrode devices adapted to be applied to, and spaced along the length of, the nerve bundle, each electrode device being capable of producing, when actuated, unidirectional electrode-generated action potentials;

and a stimulator for sequentially actuating said electrode devices with delays timed to the velocity of propagation of action potentials through the fibers of one of said diameters.

26. The apparatus according to claim 25, wherein said stimulator sequentially actuates said electrode devices to generate unidirectional action potentials producing collision blocks of the body-generated action potentials propagated through said nerve fibers of another diameter.

27. The apparatus according to claim 26, wherein said stimulator sequentially actuates said electrode devices with delays timed to the propagation velocity of larger-diameter nerve fibers to produce a "green-wave" of anodal blocks minimizing undesired blocking of said body-generated action potentials propagated through the large-diameter nerve fibers, while maximizing the generation rate of said unidirectional electrode-generated action potentials producing collision blocks with respect to the body-generated action potentials propagated through the small diameter nerve fibers.

28. The apparatus according to claim 25, wherein said nerve fibers are motor fibers of different diameters for propagating body-generated action potentials from the central nervous system to the peripheral nervous system, and said stimulator sequentially actuates said electrode devices to generate unidirectional action potentials to serve as motor action potentials to be propagated from the central nervous system to the peripheral nervous system to replace motor action potentials failed to be generated by the body.

\* \* \* \* \*